United States Patent [19]

Christian et al.

[11] Patent Number: 4,696,047
[45] Date of Patent: Sep. 22, 1987

[54] APPARATUS FOR AUTOMATICALLY INSPECTING ELECTRICAL CONNECTING PINS

[75] Inventors: Donald J. Christian, Richardson; Michael J. Stachowicz, Carrollton, both of Tex.

[73] Assignee: Texas Instruments Incorporated, Dallas, Tex.

[21] Appl. No.: 707,116

[22] Filed: Feb. 28, 1985

[51] Int. Cl.[4] .............................................. G06K 9/00
[52] U.S. Cl. ..................................... 382/8; 356/380; 356/383; 356/394; 358/106; 358/107
[58] Field of Search ................... 382/8; 356/394, 398, 356/379, 380, 383; 358/106, 107

[56] References Cited

U.S. PATENT DOCUMENTS

| 4,264,202 | 4/1981 | Guglioatta et al. | 250/262 |
| 4,398,256 | 8/1983 | Nussmeier | 382/41 |
| 4,472,056 | 9/1984 | Nakagawa et al. | 356/398 |
| 4,531,230 | 7/1985 | Brogardh | 382/65 |
| 4,550,432 | 10/1985 | Andersson | 358/107 |
| 4,553,843 | 11/1985 | Langley et al. | 356/375 |

Primary Examiner—Leo H. Boudreau
Assistant Examiner—Jose L. Couso
Attorney, Agent, or Firm—Frederick J. Telecky, Jr.; James T. Comfort; Melvin Sharp

[57] ABSTRACT

An automatic pin inspection apparatus and method inspects a plurality of pins that are arranged in a predetermined configuration such as parallel rows and converts the image of the pins to a digital signal for application to a computer system. The digital system is compared with a known reference stored in a memory within the digital computer system and units that do not meet specified tolerances are rejected. A conveyer mechanism ensures the automation of the process. A centering technique is implemented and compensates for the jittering due to the movement of pins to ensure proper alignment of the image prior to the comparison being made.

6 Claims, 8 Drawing Figures

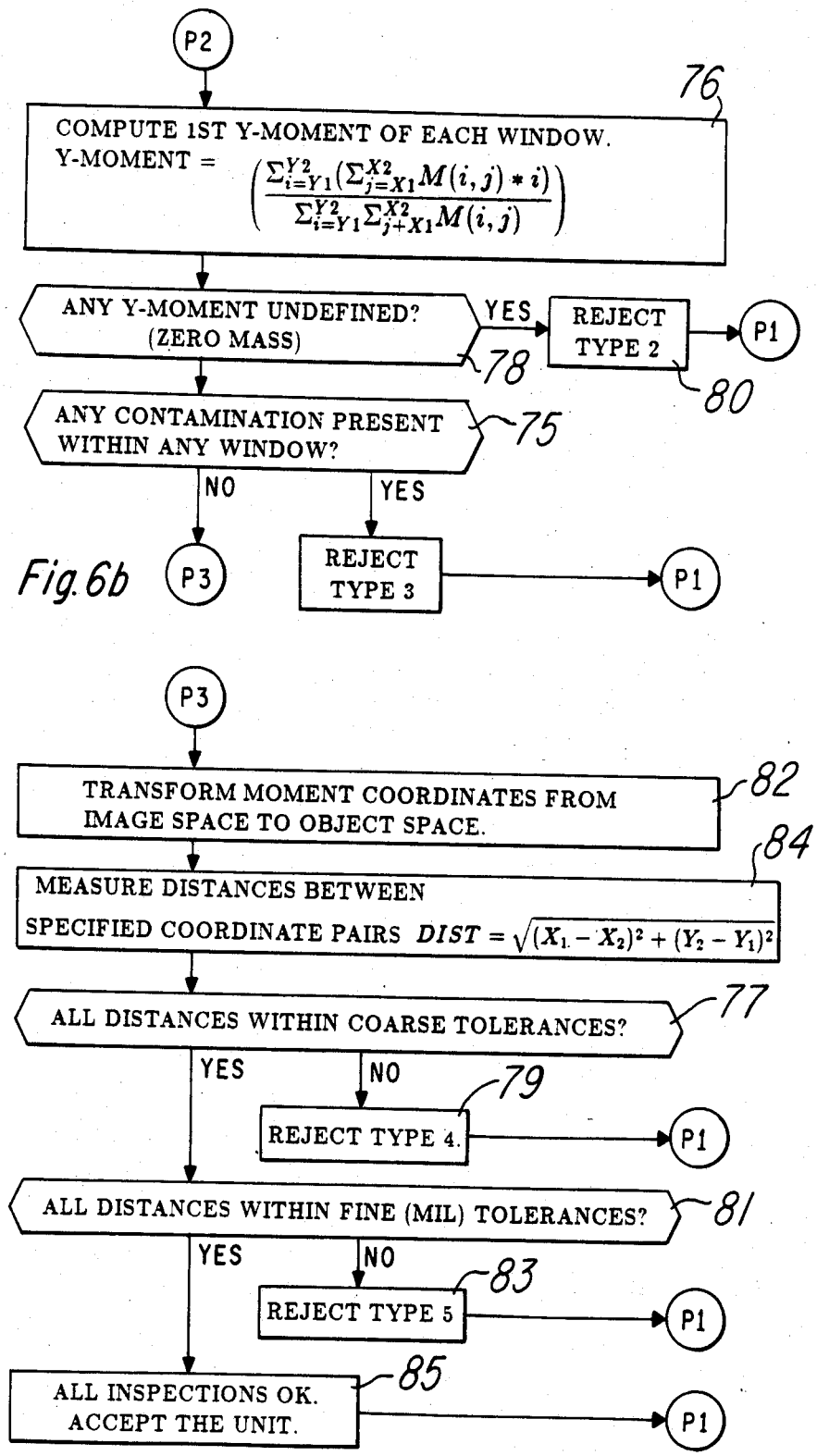

APPARATUS FOR AUTOMATICALLY INSPECTING ELECTRICAL CONNECTING PINS

BACKGROUND OF THE INVENTION

This invention relates to an apparatus and method for automatically inspecting electrical connector pins and in particular to an apparatus and method for automatically inspecting electrical connector pins for a dual inline printout electrical connector package.

The use of electrical connectors with parallel rows of pins is common in electronic interconnections such as those encountered in the manufacture and assembly of semiconductor components. Connector failures are a major cause of electrical system failures and are a major obstacle in the automation of the assembly of electronic components onto printed circuit cards or other types of assemblies.

In the semiconductor industry, electronic integrated circuits and connectors commonly use metal interconnection pins arranged in parallel rows. A common failure mode is the bending, deformation, breaking and contamination of these pins. When a unit with defective pins is assembled into a larger electronic system, it causes the larger system to fail which results in an expensive repair due to the difficulty in tracking down the defective component and replacing it. Even slightly bent pins can cause catastrophic failures. Clearly, it is better to detect and correct defective pins before they create bigger problems. Manual inspection of components and their pins has been found to be extremely tedious. Fatigue severely limits human effectiveness in making manual inspection expensive and unreliable. There is a clear need for automatic pin inspection.

An automated lead inspection system is commercially available from Synterception Incorporated, 59 El Pueblo Rd., Scotts Valley, Calif. 95066 and from Adcotech Corporation, 575 Modcourt, Sunnyvale, Calif. 54086. The precision inspection problem has been identified and discussed in publications such as the IEEE Computer Magazines, Vol. 13, No. 5, May 1980; and Vol. 15, No. 12, December 1982. However, none of the above referenced systems can detect pin presence where no missing leads are present, the straightness of pins where the pins are not bent past predetermined limits, the lengths of pins where pins are too short or too long and the overall dimensions of the pins where the diameter is within tolerance.

SUMMARY OF THE INVENTION

An automatic pin inspection apparatus and method inspects a plurality of pins that are arranged in a predetermined configuration such as parallel rows and converts the image of the pins to a digital signal for application to a computer system. The digital system is compared with a known reference stored in a memory within the digital computer system and units that do not meet specified tolerances are rejected. A conveyer mechanism ensures the automation of the process. A centering technique that is implemented and compensates for the jittering due to the movement of pins to ensure proper alignment of the image prior to the comparison being made.

It is the object of the invention to provide a method and apparatus for automatically detecting any missing pins from an electronic package;

It is another object of the invention to detect the presence of extra pins on an electronic package;

It is yet another object of the invention to measure for the straightness of pins that are part of an electronic package;

It is still another object of the invention to measure the length of the pins of the electrical connectors and to reject connectors that have leads that are too long or too short; and it is still another object of the invention to measure pin dimensions to ensure that the diameters of the pins of the electrical connectors are within predetermined tolerances.

These advantages and objects of the invention will be more apparent from the reading of the specification in conjunction with the figures in which:

BRIEF DESCRIPTION OF THE FIGURES

FIGS. 6A–6C is a flow diagram of the processes implemented by the apparatus of FIG. 1.

DETAILED DESCRIPTION OF THE EMBODIMENTS

Figure 1:
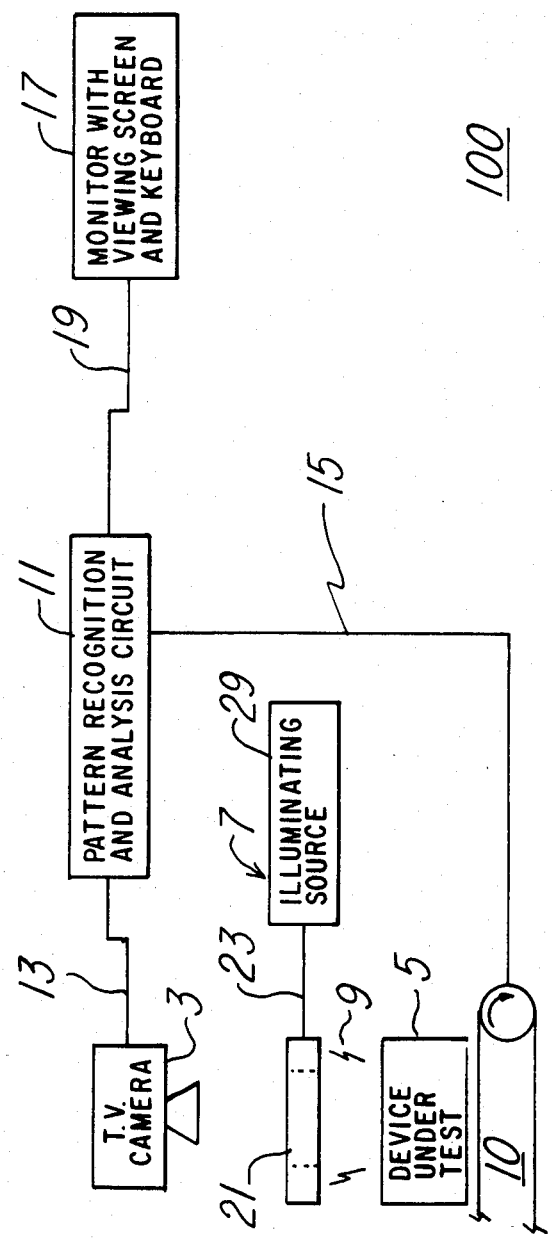
FIG. 1 is a block diagram of an automatic pin inspection system according to the invention.

In FIG. 1 to which reference should now be made, there is shown a block diagram of an apparatus 100 automatically inspecting electrical connector pins. The apparatus 100, being it is automatic includes a controllable article conveyer mechanism 10 such as that disclosed in U.S. Pat. No. 4,498,574 assigned to Texas Instruments Incorporated incorporated herein by reference. The article conveyer mechanism 10 positions under a TV camera 3 the connector or article under inspection 5. Where the apparatus 100 is used to inspect dual inline packages, then the connector under inspection 5 is brought in alignment with the TV camera 3 with the pin tips pointing directly toward the TV camera 3. An illuminating system 7 provides light 9 to the connector under inspection 5. The tips of the pins of the connector under inspection are illuminated for imaging by the TV camera 3 which provides an electrical signal to the pattern recognition and analysis circuit 11 via video line 13. The pattern recognition and analysis circuit 11 decomposes the image that is provided by it by the TV camera 3 and compares it against preset tolerances and based upon this information the connector under test is either accepted or rejected by a signal that is applied to the conveyor mechanism 10 via data line 15. An operator has the ability to view the images by a TV monitor 17 which is connected to the pattern recognition and analysis circuit 11 by data lines 19. Additionally, a keyboard is included with the monitor and is provided for entering defined tolerances beyond which a connector under inspection 5 can be rejected, and for entering data to control the operation of the pattern recognition and analysis circuit 11.

Figure 2:
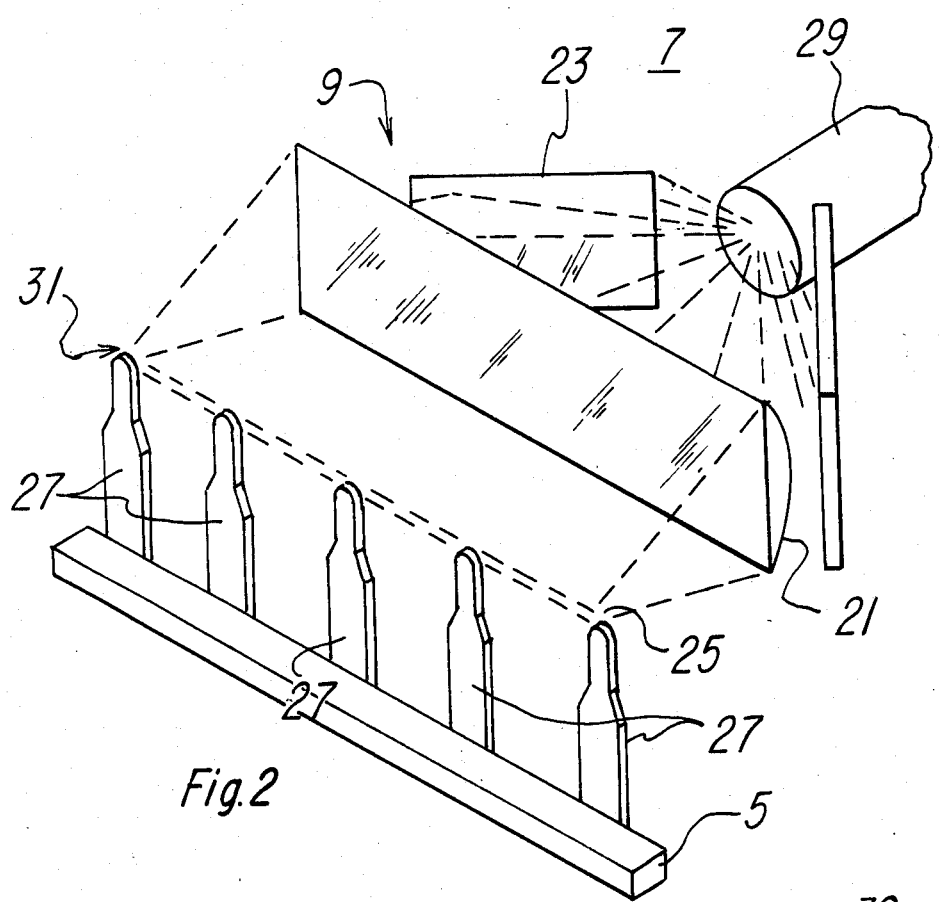
FIG. 2 is an illustration of the illuminating system of the inspection assembly of FIG. 1.

In FIG. 2, a partially sectioned connector under test 5 is illustrated with a plurality of pins 27 pointing toward the TV camera 3. The illuminating system 7 includes a light source 29 that generates light that is carried to a lens 21 via a bifurcated bundle of fiber optics 23. The bifurcated bundle 23 applies the light to a lens 21 which causes the tips 25 of the pins 27 to be illuminated by a single plane of light 31. The illumination of only the tips 25 by a plane of light 31 facilitates the pattern recognition of the pin arrangements that are a portion of the connector under test 5. Pin tips of pins that are too long or too short are not illuminated by the plane of light 31.

Figure 3:
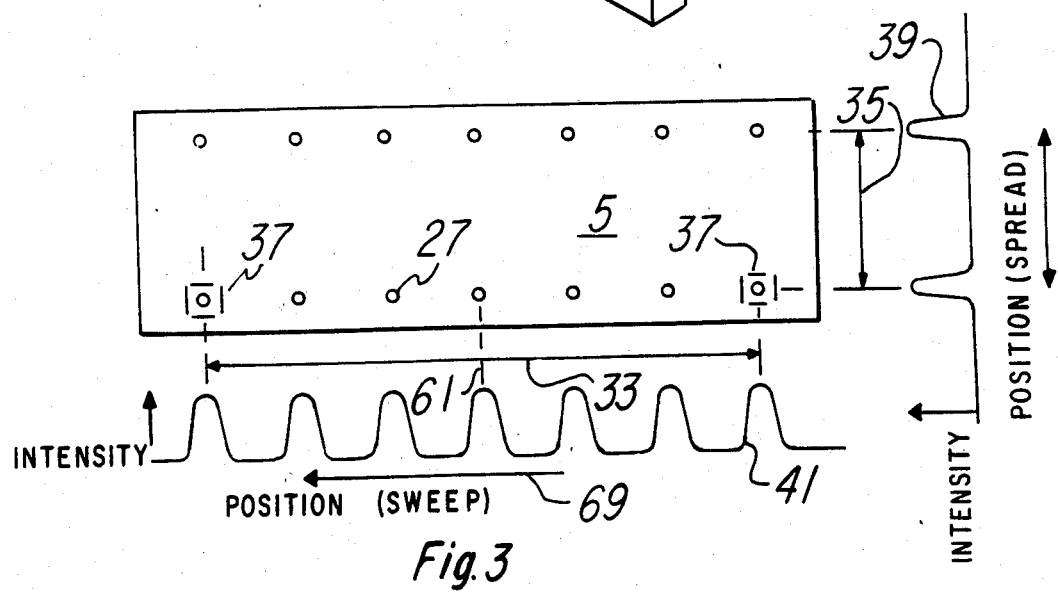
FIG. 3 is an illustration of a pattern recognition of the apparatus of FIG. 1.

FIG. 3 shows a view of the connector under test 5. The pins 27 are arranged in a predetermined configuration according to rows as indicated by the sweep arrow 33 and columns as indicated by the spread arrow 35. Each pin 27 in the preferred embodiment, is assigned by a window 37 in which the pattern recognition and analysis circuit 11 attempts to locate by isolation a pin 27. The TV camera 3 is able to obtain light intensity in both the sweep and spread dimension as a function of position versus light intensity as indicated by the column spectrum waveform 39 and the row spectrum waveform 41. The pattern recognition and analysis circuit 11 can find the centroid 67 of each pin and identify all in accordance with connector specifications such as the military specification MIL-883B. Once a first pin 27 has been isolated and identified, and knowing the expected distance between the pins, it is easy to identify the location of all the pins and to compensate for variations of pin position due to pin bending and jitter of the article conveyer mechanism 1 or the imprecise alignment of the component under inspection 5 with respect to the TV camera 3. A threshold is established above which the intensity of light as included in waveforms 39 and 41 is treated as a logic "1" and the background is treated as a logic "0". This creates a lighted area with a dark background that facilitates both pattern recognition and analysis.

There are four basic functions provided by the pin inspection apparatus 100 of FIG. 1. One, it locates the position of the device under test 5 as is represented on the video signal line 13 and isolates patterns of logic "1's". Secondly, after the pattern is isolated within the picture, each individual pin is located and the distances between pins are then measured and finally the distance between each pin pair is compared against a predefined tolerance.

It should be noted that the memory unit 26 is arranged as a two-dimensional array of picture elements. Each element can have one of two states. One indicating light intensity greater than the present threshold that is set by the microprocessor 6 providing data to the D/A converter 216 for comparison by the comparator 116 and zero indicating light intensity less than the predetermined threshold. The illuminating source 29 illuminates or highlights only the pin tips. When this highlighted image is inputted and processed and stored in the memory unit 26, it appears as a cluster of ones representing pins in a matrix of zeros representing the backgrounds. Each pin cluster is considered individually and isolated in a window boundary 37. After registration of a cluster, a rectangular window 37 is constructed which encloses the cluster and some of the surrounding area. The first moment of inertia of the windows is obtained giving equal positive weights to all "1" memory cells and no weight to all "0" memory cells. The first moment of each pin cluster is computed and stored in a memory table within the memory 26 provided for this purpose. Each moment is represented by a two-dimensional coordiante specifying image position in both X and Y directions or sweep and spread directions to an accuracy that is equal to 1/16th of the distance between adjacent memory cells. After the pin clusters are located, the distance between each pin pair is obtained. The generated memory table contains the first moment of inertia for each pin cluster image. A second table is generated representing coordinate straight line distances between certain pairs of pins. Specifications of the distance are published in previously discussed documents.

In the case of dual inline packages, measurements must be made between each vertically aligned pair and betwen each pin and its extreme leftmost horizontal neighbor. Each pair distance is transformed from the memory image space back to physical space by a linear scale operatin that is implemented within the microprocessor 6. This is analogous to projection from the camera image plane to the object image plane. The value of the scalar transform constants are a function of camera lens magnification, video clock rate and other factors. Selection of scalars is made automatically during calibration procedures and the scalars remain constant while the pin inspecting apparatus 100 is in operation. Once the physical distance between pin pairs is known, they can be compared with preset nominal values, and judged to be either within preset tolerance or exceeding preset tolerance. Specifications for both nominal values and tolerances are published for example, in Mil-Spec 883B as well as other documents. These criteria define absolute measurements for bending and deformation allowances.

Figure 6A:
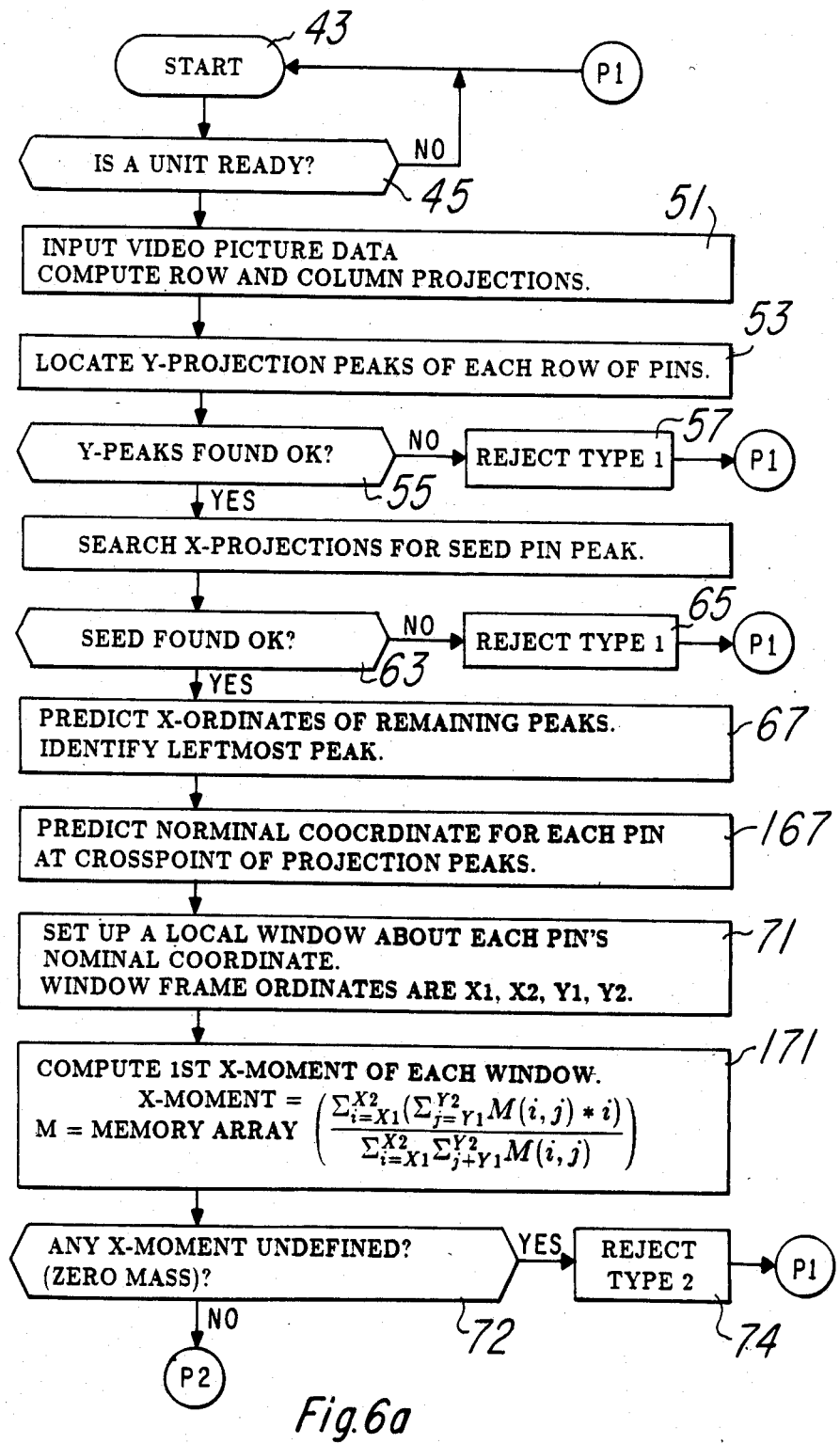

FIGS. 6A-6C to which reference shoudl now be made is a logic flow diagram of the pin inspection apparatus 100 in which the starting point is at block 43. Decision block 45 ascertains if a connector 5 is ready to be inspected. This is dependent upon the operation of the article conveyor mechanism 10 among other things. If no unit is ready, then the "no" line is taken and if a connector under inspection 5 is ready, then the "yes" line is taken where at block 51 the TV camera 3 of FIG. 1 will input video picture data and the pattern recognition and analysis circuit 11 will compute the row and column projections based upon the intensity of the reflected light picked up by the TV cameras as indicated by the waveforms 39 and 41. At this point it should be noted that row projections are designated by ordinates of Y and column projections are designated by X ordinates. After the completion of the row and column projections at block 51, the Y projection peaks of each row of pins are located at block 53. Decision block 55 ascertains if the Y peaks are found okay. If they are not, then the connector under inspection 5 is rejected and this indicates that there are missing pins and the pattern recognition analysis circuit 11 returns to the start position 43. If the Y peaks are found okay, then the column projections for a seed pin peak 61 is searched for at block 59. The seed (center) peak 61 is shown in FIG. 3. The seed peak 61 which once identified enables the pattern recognition analysis circuit 11 to count in each direction to predict the expected X ordinates of the remaining pins. Decision block 63 ascertains if a seed peak has been found. If none is found, then at block 65, the unit under test is rejected and the pattern recognition and analysis circuit 11 returns to the start position 43. If one is found, then at blocks 67 and 167 a prediction ismade on the position of the other pin pairs to the left of the seed peak 61 as indicated by arrow 69 in FIG.

3. The positions are searched for the presence of peaks until the leftmost peak is found. At block 71 individual search windows 37 for each pin are set up and the first moment of each search window is computed. In both the X and Y dimensions, each moment pair represents the cluster's XY coordinate. Any unfound moment results in rejection of the device at decision block 72 and block 74. The Y moment is computed at block 76 and if any Y moments are not found then at decision block 78 and block 80 the device is rejected. At decision block 75, any contamination such as that obtained by having a solder blob or plate flake on the tip of a pin 27 is measured and if that contamination is present then that unit under inspection is rejected and the pattern recognition analysis circuit returns to the start position 43. The pixel distance as is detected and stored is changed to physical distance at block 82 and the distance between pins is obtained at block 84. If no contamination is detected, then at decision block 77 a test is made to ensure that all measurements are within coarse tolerances. If the measurements fail to meet the coarse tolerances, then that unit is rejected at block 79 and the pattern recognition and analysis circuit returns to start position 43. If the coarse tolerances are met, then the measurements are compared with the fine tolerances at block 81 and if they are not met, then the connector under test 5 is rejected at block 83. If all inspections are okay, then at block 85, the unit is ready to accept the second unit under test. Bear in mind that the coarse tolerances at block 77 may be the only requirements for the connector and that devices at that point may be acceptable for the purposes for which they are intended. However, the two-step test method as disclosed here enables the automatic pin inspector 100 to insure tolerances heretofore unattainable.

Figure 4:
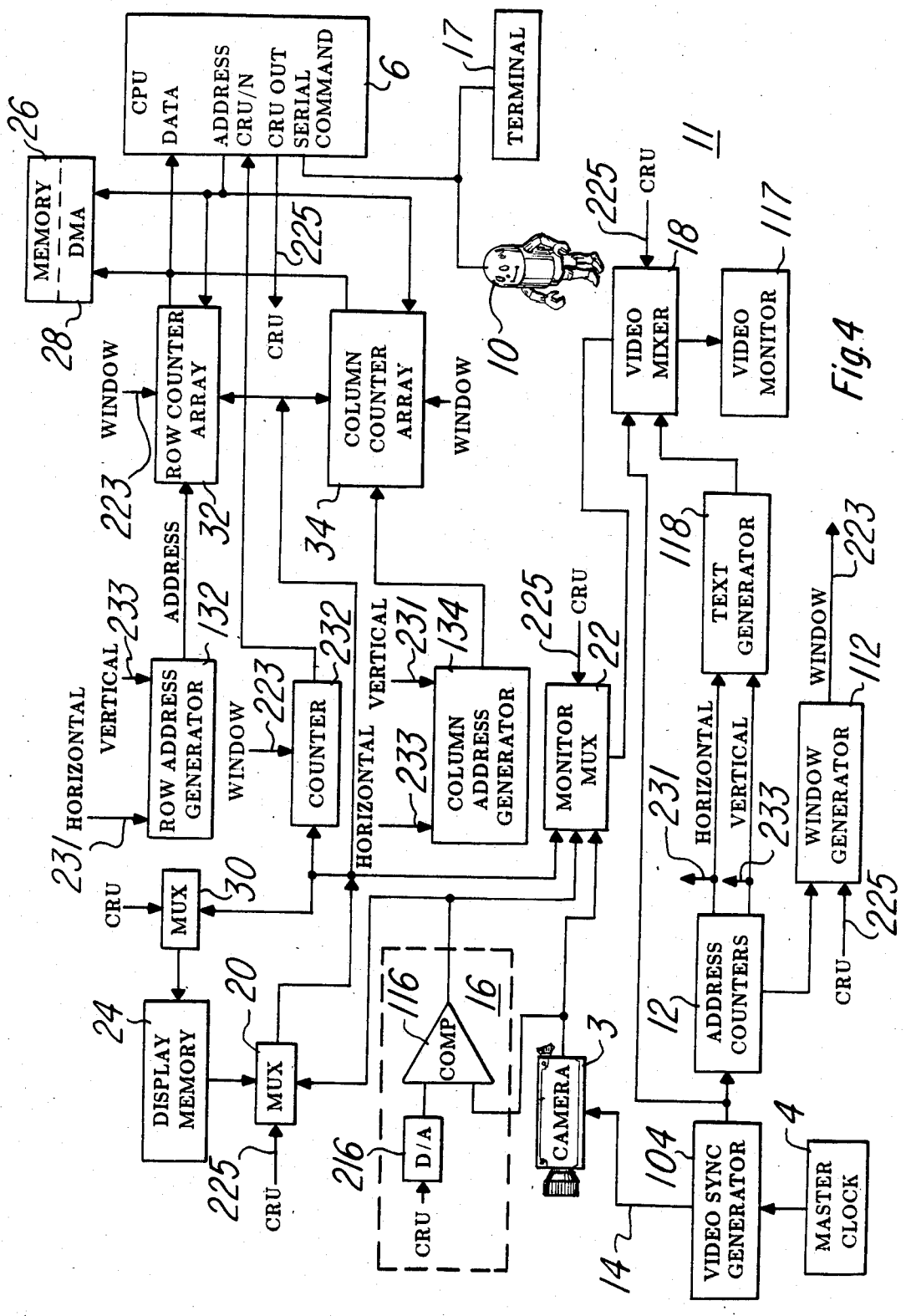
FIG. 4 is a block diagram of the analysis circuit of FIG. 1.

FIG. 4 is a block diagram of the pattern recognition and analysis circuit 11 as well as the TV camera 3 and includes a microprocessor 6 which provides control signals to the video processing circuityry as well as to the TV camera 3 in the form of CRU lines via data bus 8. The monitor 117 and keypad (terminal 17) are provided to allow control of the apparatus and to allow setup and verification of operation. Additionally, the handling of the unit under inspection 5 may be implemented through the use of anintelligent robot at 10. The video 3 camera is synchronized by a signal that is provided from the 16 megahertz clock 4 which additionally provides clocks to horizontal address counters and a vertical address counter of the address counters 12 and to the text generator 118. Again, the window generator 112 and text generator 118 are under the control of the microprocessor 6. Coming from the 16 megahertz clock 4 in a sync signal on line 14 which is applied to the camera 3 and a video output from the camera 3 is applied to a video input threshold and comparator circuit 16 that includes a comparator 116 and digital to analog converter 216. The video input threshold is provided by comparator circuit 16 which provides an analog video signal to the video mixer 18 which drives the video monitor 117 and is under the control of microprocessor 6, the text generator 118, sync from the conductor 14 and the text generator 118.

The threshold is established by the microprocessor 6 through digital commands provided from the CRU (Control Register Unit) to the D/A 16. This threshold provides for a dark or black background and a lighted or light pin tips in a digital or binary form. This was discussed in conjunction with FIG. 3. Additionally binary picture data is applied to a memory unit 26 via direct memory access logic 28. The picture data is also fed into a display memory 24 via input mux 20, as well as into direct memory controller 28 which controls the transfer of picture data from the display memory 24 to the multiplexer 20. There is a row counter array 32 which provides the row and column summation vectors and a column array 34 that provide for column summation vectors.

The address counters 12 provide horizontal and vertical advance signals to a row address generator 132 and a column address generator 134 which are used to provide row and column addresses to the row counter array 32 and column counter array 34 which are used to store the binary video data in the memory device 26 according to addresses that relate to the raster scan position of the camera 3.

Counter 232 is used to integrate across the entire area of the window 37 and yields the sum total of all bright objects which are within window 37.

Figure 5:
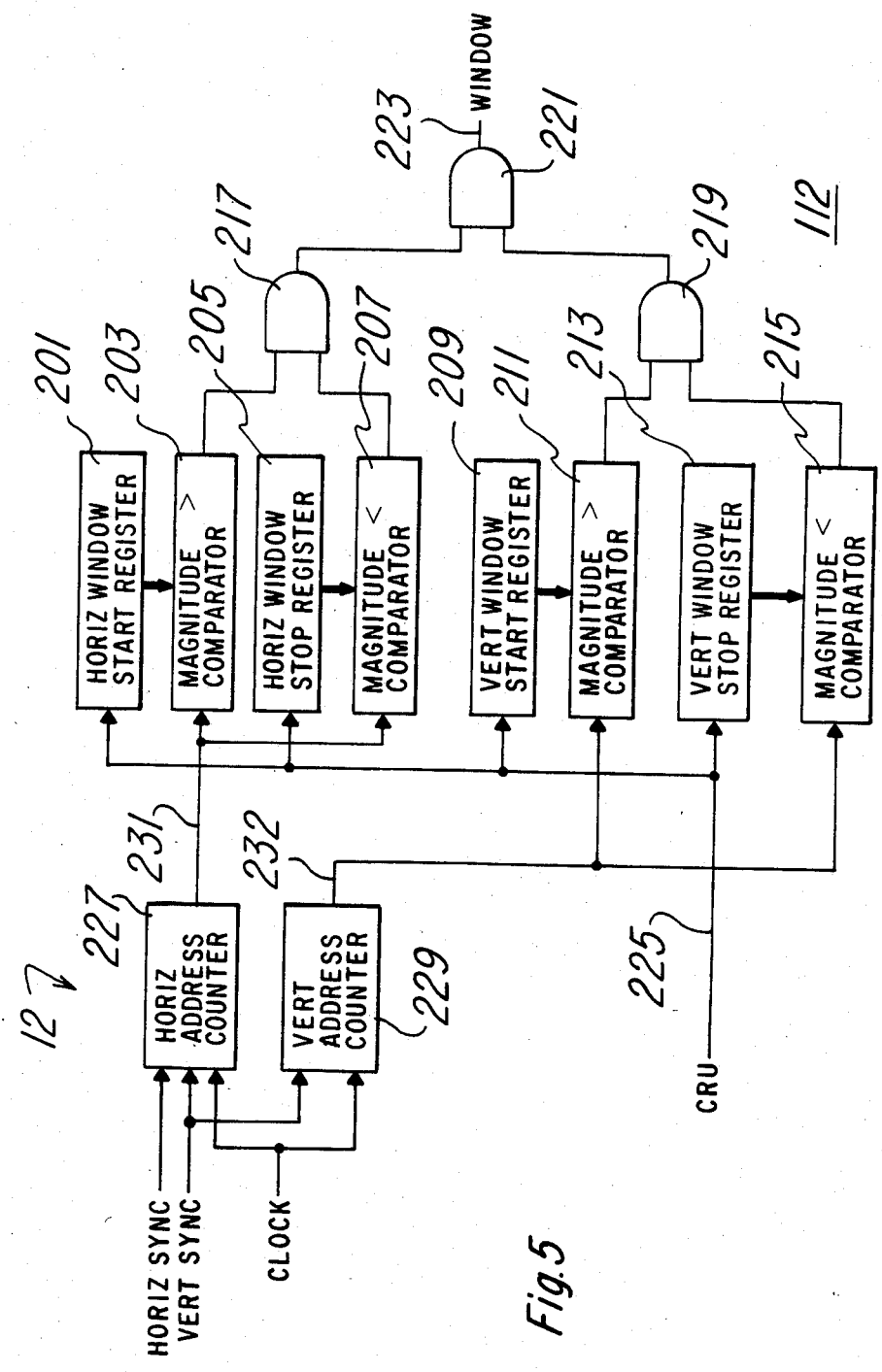
FIG. 5 is a block diagram of the window generator of FIG. 4.

FIG. 5 which should be used in conjunction with FIG. 4 is a more detailed block diagram of the address counters 12 and the window generator 112. The address counter 12 includes a horizontal address counter 27 which counts the clock pulses per line and provides the position of the scan of the video camera 3 on a line and is reset at the end of each line of sweep that is made by the video camera and additionally at the end of each frame when the vertical sync comes in. The vertical address counter 229 identifies the vertical position of the sweep by counting the number of clock pulses between vertical sync pulses. This information is applied in FIG. 4 to the row address generator 132 and the column address generator 134 as well as to a text generator 118 in addition to the window generator 112. The window generator 112 establishes a window 37 that is swept across both in the sweep and the spread direction of the device under test 5 as is shown in FIG. 3 and is generated by loading into a horizontal window start register 201, a horizontal window stop register 205, a vertical window start register 209, a vertical window stop register 213, data which corresponds to the expected count in the horizontal address counter 227 and the vertical address counter 229 or the sweep of the video camera 3 when the sweep is within the window 37. This information is provided to the appropriate registers from the controlled register unit of the CPU 6 via data bus 225. The contents of the horizontal address counter are applied to a greater than magnitude comparator 203 and a less than a magnitude comparator 207. The greater than magnitude comparator 203 compares the contents of the data that is stored in the horizontal window start register 201 with the output contents of the horizontal address counter 231 and when the contents of the horizontal address counter 231 is greater than the contents of the horizontal start register 201, then a logic "1" is applied to AND gate 217. Similarly, as long as the contents of the horizontal address counter 227 is less than the contents of the horizontal window stop register 205 in the output of the less than magnitude comparator 207 will be a logic "1". In a similar manner, the contents of the vertical address counter 229 are compared to the contents of the vertical window start register 209 by a greater than magnitude comparator 211 and a less than magnitude comparator 215 compares the contents of the vertical address counter 229 to the contents of the vertical window stop register 213. The magnitude comparators are combined by AND gate 219 and the outputs of the AND gates 217 and 219 are combined by AND gate 221 given an logic "1" on conductor 223 during the period of time that the scan of the video camera 3 is located within the window that is defined by the CPU 6 loading position information into the start and stop registers that are both vertical and horizontal and are contained within the window generator 112.

Although the invention has been described with some detail, it is obvious to one skilled in the art that the invention is defined by the scope of the appended claims.

What is claimed is:

1. A pin inspection system for inspecting a plurality of pins tips arranged in a predetermined configuration comprising:
   illuminating means for illuminating the tips only, of pins which are of correct length, and which do not illuminate the tips of pins which are too long or too short;
   video camera means for obtaining a video image of the illuminated pin tips by sweeping in a raster scan fashion the pin tips to obtain a first waveform representing light intensity versus relationship to the raster scan position;
   a comparator for comparing the first waveform to a predetermined threshold and to provide a first logic state when the amplitude of the waveform is about the predetermined threshold and a second logic state when the amplitude of the first waveform is below the predetermined threshold;
   memory means for arranging the first and second logic states according to the raster scan position;
   summation means for locating clusters of the first logic states in both the row and column directions of the memory means;
   isolation means for isolating clusters in the first logic state;
   inertia measuring means for locating the first moment of inertia for each of the isolated clusters of the first logic state to obtain a first coordinate for each cluster;
   transformation means for transforming the first coordinates to physical distances;
   comparator means for comparing the physical distance to a predetermined criterion; and
   classifying according to the results of the comparison the transform coordinates to obtain the results of the pin tips inspection.

2. The pins inspection system according to claim 1 wherein the illuminating means comprises:
   means for providing a source of light;
   means for transporting the light from the source of light means to the pin tip; and
   means for focusing the light on the plurality of pin tips.

3. The pin inspection system according to claim 2 wherein the transport means comprises:
   a bifurcated bundle of optical fibers.

4. The pin inspection system according to claim 1 wherein the plurality of pins are arranged in rows and columns and the video camera means comprises:
   means for performing row projections on the image of the plurality of pin tips; and
   means for performing column projections on the image of the plurality of pin tips.

5. A method of inspecting a plurality of pin tips arranged in a predetermined configuration for presence, straightness and contamination comprises:
   illuminating the tips only, of pins which are of correct length, and not illuminating the tips of pins which are too long or too short;
   attaining a video image of the illuminated pin tips by sweeping in a raster scan fashion the pin tips to obtain a first waveform representing light intensity in relationship to the raster scan position;
   comparing the waveform to a predetermined threshold and to provide a first logic state when the amplitude of the first waveform is above the threshold and to provide a second logic state when the amplitude of the waveform is below the predetermined threshold;
   arranging the first and second logic states according to raster scan position;
   locating clusters of the first logic states in both the first and second direction;
   isolating the clusters of the first logic states;
   finding the first moment f inertia of the isolated clusters of the first logic state in a first and second direction to obtain a first coordinates for each cluster;
   transforming the coordinates to physical distances;
   comparing the physical distance to a predetermined criteria; and
   classifying the results of the comparison to obtain the results of the pin inspection method.

6. The method according to claim 5 wherein the steps of illuminating the pins tips further comprises the steps of:
   providing a source of light;
   transporting the light from the light source to the pin tips; and
   focusing the light on the plurality of pin tips.

* * * * *